United States Patent
Malik et al.

(10) Patent No.: US 6,908,923 B2
(45) Date of Patent: Jun. 21, 2005

(54) COMPOSITIONS AND METHODS FOR TREATING HEART FAILURE

(75) Inventors: Fady Malik, Burlingame, CA (US); Adam Lewis Tomasi, San Francisco, CA (US); Bainian Feng, Foster City, CA (US); Erica Anne Kraynack, Belmont, CA (US); Kathleen A. Elias, San Francisco, CA (US); Pu-Ping Lu, Foster City, CA (US); Whitney Walter Smith, El Cerrito, CA (US); Xiangping Qian, Foster City, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 77 days.

(21) Appl. No.: 10/327,219

(22) Filed: Dec. 20, 2002

(65) Prior Publication Data

US 2003/0158233 A1 Aug. 21, 2003

Related U.S. Application Data

(60) Provisional application No. 60/343,088, filed on Dec. 21, 2001.

(51) Int. Cl.$^7$ .................. A61K 31/4965; A61K 31/44; A61K 31/42; A01N 43/40; A01N 43/80
(52) U.S. Cl. ................. 514/255.05; 514/335; 514/345; 514/339; 514/340; 514/378; 514/448; 514/622; 544/405; 546/261; 546/268.4; 546/272.1; 546/277.4; 546/300; 548/248; 549/72; 564/184
(58) Field of Search .................. 544/405; 546/261, 546/268.4, 272.1, 277.4, 300, 262, 290, 316; 548/248; 549/72; 564/184; 514/255.05, 335, 345, 339, 340, 378, 448, 622

(56) References Cited

U.S. PATENT DOCUMENTS

| | | | |
|---|---|---|---|
| 3,055,905 A | 9/1962 | Graf et al. ............. 260/294.8 |
| 3,448,029 A | * 6/1969 | Weinberger ............. 204/181 |
| 3,674,850 A | 7/1972 | Osborne ............. 260/559 S |
| 3,862,088 A | 1/1975 | Wolf et al. |
| 4,783,472 A | 11/1988 | Fabre et al. ............. 514/338 |
| 6,001,379 A | 12/1999 | Griat ............. 424/401 |
| 6,001,879 A | 12/1999 | Seitz et al. |
| 6,143,764 A | 11/2000 | Kubo et al. ............. 514/312 |
| 6,207,829 B1 | 3/2001 | Dunn et al. ............. 544/262 |
| 6,355,660 B1 | 3/2002 | Ricks et al. ............. 514/357 |
| 6,410,254 B1 | 6/2002 | Finer et al. |
| 6,495,337 B1 | 12/2002 | Hartman et al. |
| 6,521,622 B1 | 2/2003 | Ricks et al. ............. 514/252.01 |
| 6,548,549 B1 | 4/2003 | Seitz et al. ............. 514/619 |
| 6,706,740 B2 | 3/2004 | Ricks et al. ............. 514/357 |

FOREIGN PATENT DOCUMENTS

| | | |
|---|---|---|
| DE | 31 39 457 A1 * | 4/1983 |
| DE | 2000-10010002 | 9/2001 |
| JP | 58-74665 | 5/1983 |
| JP | 2-115839 | 4/1990 |
| JP | 2-196769 A | 8/1990 |
| JP | 3-292327 | 12/1991 |
| JP | 05043556 | 2/1993 |
| WO | WO 93/17027 A1 | 9/1993 |
| WO | WO 99/41239 * | 8/1999 |
| WO | WO 01/14339 A2 | 3/2001 |
| WO | WO 01/64773 A1 | 9/2001 |
| WO | WO 03/037900 A2 | 5/2003 |
| WO | WO 03/059258 A2 | 7/2003 |
| WO | WO 03/103654 A1 | 12/2003 |
| WO | WO 03/103655 A1 | 12/2003 |
| WO | WO 03/103657 A1 | 12/2003 |
| WO | WO 2004/001058 A2 | 12/2003 |

OTHER PUBLICATIONS

Hawley's Condensed Chemical Dictionary, 12th ed., Richard J. Lewis, Sr., © 1993 by Van Nostrand Reinhold. p. 594.*

Concise Chemical Dictionary, edited by Drs. Hans–Dieter Jakubke and Hans Jeschkeit, © 1993 by Walter de Gruyter & Co., p. 490.*

McGraw–Hill Dictionary of Chemical Terms, 3rd ed. edited by Sybil P. Parker, © 1984 McGraw–Hill, Inc., p. 200.*

Zlotin et al. (2000) J. Org. Chem. 65(25), 8430–8438.

Shkinyova et al. (2000) Tetrahedron Letters 41(25), 4973–4975.

Shevelev et al. (1995) Mendeleev Commun. (1995), (4), 157–8.

Chemcats Copyright 2004 ACS on STN, Registry No. 332035–74–2 "Benzamide, 4–[methyl(phenylsulfonyl)amino]–N–3–pyridinyl–."

Chemcats Copyright 2004 ACS on STN, 2004:1448030 Chemcats, ChemBridge Screening Library, May 19, 2004, Order No. 5734271, "4–[methyl(phenylsulfonyl)amino]–N–3–pyridinylbenzamide," 332035–74–2.

Chemcats Copyright 2004 ACS on STN, 2003:2676485 Chemcats, TimTec Overseas Stock, May 19, 2003, Order No. OVS1270658, "Benzamide, 4–[methyl(phenylsulfonyl)amino]–N–3–pyridinyl–," 332035–74–2.

(Continued)

Primary Examiner—Mukund J. Shah
Assistant Examiner—Zachary C. Tucker
(74) Attorney, Agent, or Firm—Finnegan, Henderson, Farabow, Garrett & Dunner, L.L.P.

(57) ABSTRACT

Certain substituted benzamide derivatives of Formula I:

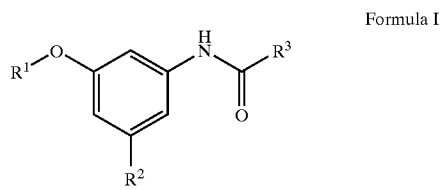

selectively modulate the cardiac sarcomere, for example by potentiating cardiac myosin, and are useful in the treatment of systolic heart failure including congestive heart failure.

43 Claims, No Drawings

OTHER PUBLICATIONS

Chemcats Copyright 2004 ACS on STN, 2003:2118551 Chemcats, AsInEx Express Gold Collection, Apr. 23, 2003, Order No. BAS 1979659, " Benzamide, 4-[methyl(phenylsulfonyl)amino]-N-3-pyridinyl-," 332035-74-2.

Chemcats Copyright 2004 ACS on STN, 2003: 621761 Chemcats, Ambinter Screening Library, Jan. 1, 2004, Order No. 139969372, " Benzamide, 4-[methyl(phenylsulfonyl)amino]-N-3-pyridinyl-," 332035-74-2.

Chemcats Copyright 2004 ACS on STN, 2002: 2006761 Chemcats, Interchim Intermediates, Jul. 9, 2002, Order No. BAS 1979659, " Benzamide, 4-[methyl(phenylsulfonyl)amino]-N-3-pyridinyl-," 332035-74-2.

Kubo et al., 2003, "Synthesis and structure activity relationship for new series of 4-Phenoxyquinoline derivatives as specific inhibitors of platelet-derived growth factor receptor tyrosine kinase," Bioorganic & Medicinal Chemistry, 11(23):5117-5133.

Künzle et al. 1969, "70. Dibenz[b,f]-1, 4-oxazepin-11(10$H$)-one und Dibenz[b,e]-1, 4-oxazepin-11(5$H$)-one," Helvetica Chimica Acta, 52: 622-628. (translation of abstract on p. 622).

"207 Registry Compounds Not Indexed in Chemical Abstracts (Free Scan Str Format)" Copyright 2004 ACS on STN.

* cited by examiner

COMPOSITIONS AND METHODS FOR TREATING HEART FAILURE

CROSS-REFERENCE TO RELATED APPLICATONS

This application claims the benefit of co-pending provisional U.S. Application Ser. No. 60/343,088, filed Dec. 21, 2001, incorporated herein by reference.

STATEMENT OF GOVERNMENT INTEREST

This invention was made with government support under NIH Grant Number 1 R43 HL66647-01. Accordingly, the United States Government may have certain rights in this invention.

FIELD OF THE INVENTION

The invention relates to substituted benzamide derivatives, particularly to compounds that selectively modulate the cardiac sarcomere, and specifically to compounds, pharmaceutical formulations and methods of treatment for systolic heart failure, including congestive heart failure.

BACKGROUND OF THE INVENTION

THE CARDIAC SARCOMERE

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation (Robbins J and Leinwand L A. (1999) *Molecular Basis of Cardiovascular Disease*, Chapter 8. editor Chien, K. R., W. B. Saunders, Philadelphia). Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes (Goodson H V and Spudich J A. (1993) Proc. Natl. Acad. Sci. USA 90:659–663). Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound (Spudich J A. (2001) Nat Rev Mol Cell Biol. 2(5):387–92). Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized (Robbins, supra). The beta form is the predominant form (>90 percent) in adult human cardiac muscle. Both have been observed to be regulated in human heart failure conditions at both transcriptional and translational levels (Miyata supra), with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

HEART FAILURE

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 957,000 (in 1997) making CHF the most common discharge diagnosis in people age 65 and over. The five-year mortality from CHF approaches 50% (Levy D. (2002) New Engl J Med. 347(18):1442–4). Hence, while therapies for heart disease have greatly improved and life expectancies have extended over the last several years, new and better therapies continue to be sought, particularly for CHF.

"Acute" congestive heart failure (also known as acute "decompensated" heart failure) involves a precipitous drop in heart function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases heart function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases heart function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

THERAPEUTIC ACTIVE AGENTS

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Given the limitations of current agents, new approaches are needed to improve cardiac function in congestive heart failure. The most recently approved short-term intravenous agent, milrinone, is now nearly fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes. The selectivity of agents directed at the cardiac sarcomere (for example, by targeting cardiac beta myosin) will be an important means to achieve this improved therapeutic index. The present invention provides such agents (particularly sarcomere activating agents) and methods for their identification and use.

SUMMARY OF THE INVENTION

The present invention provides compounds, pharmaceutical compositions and methods for the treatment of heart disease including CHF, particularly systolic heart failure. The compositions are selective modulators of the cardiac sarcomere, for example potentiating cardiac myosin.

In one aspect, the invention relates to Formula I:

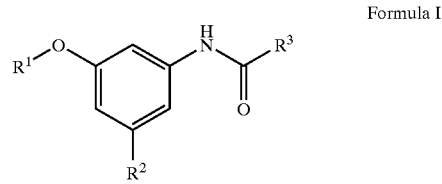

Formula I wherein:
$R^1$ is alkyl, substituted alkyl, aryl, substituted aryl, heteroaryl, and substituted heteroaryl;
$R^2$ is acetyl, acetylamino, acetylene, alkoxycarbonyl, carboxamido, cyano, halo, heteroaryl, hydrogen, nitrile, nitro, and trifluoromethyl; and
$R^3$ is aryl, substituted aryl, heteroaryl, and substituted heteroaryl;
including single stereoisomers, mixtures of stereoisomers, and the pharmaceutically acceptable salts thereof. The compounds of Formula I are useful as active agents in practice of the methods of treatment and in manufacture of the pharmaceutical formulations of the invention, and as intermediates in the synthesis of such active agents.

In another aspect, the invention relates to compounds represented by Formula I, wherein:
$R^1$ is alkyl, substituted alkyl, aryl, substituted aryl, heteroaryl and substituted heteroaryl;
$R^2$ is acetyl, acetylamino, acetylene, alkoxycarbonyl, carboxamido, cyano, halo, heteroaryl, hydrogen, nitrile, and trifluoromethyl; and
$R^3$ is aryl, substituted aryl, heteroaryl, and substituted heteroaryl;
or a single stereoisomer, or mixture of stereoisomers, or a pharmaceutically acceptable salt thereof. Preferred in this aspect are those compounds. isomers and salts where:
$R^1$ is optionally substituted aryl or heteroaryl, preferably phenyl, substituted phenyl or pyridinyl (especially 3-chlorophenyl, 4-fluorophenyl, 4-hydroxyphenyl, 3-methylphenyl, pyridin-2-yl, pyridin-3-yl or pyridin-4-yl);
$R^2$ is acetyl, acetylene, alkoxycarbonyl, cyano, halo, heteroaryl, hydrogen or trifluoromethyl (especially acetylene, cyano, ethoxycarbonyl, fluoro, hydrogen, oxazol-2-yl, pyridin-2-yl, pyrimidin-2-yl, thiazol-2-yl or trifluoromethyl); and
$R^3$ is phenyl, optionally substituted with lower alkoxy, lower alkyl, halo, hydroxy, hydroxy-lower alkyl or nitro, or $R^3$ is benzodioxolyl, furanyl, indolyl, isoxazolyl, pyrazolyl, pyridinyl or thiophenyl, optionally substituted with lower alkyl, lower alkoxy, or halo (especially 3-hydroxyphenyl, 4-hydroxyphenyl, 4-fluorophenyl, isoxazol-5-yl, pyridin-3-yl, pyridin-4-yl, thiophen-2-yl or 5-methyl-thiophen-2-yl).

In still another aspect, the invention relates to compounds represented by Formula I, wherein:
$R^1$ is alkyl, substituted alkyl, aryl, substituted aryl, heteroaryl, or substituted heteroaryl;

$R^2$ is nitro; and $R^3$ is aryl, substituted aryl, heteroaryl or substituted heteroaryl;

provided that:

when $R^1$ is pyridin-3-yl, $R^3$ is not 3-bromophenyl, 3-fluorophenyl, 4-fluorophenyl, furan-2-yl, 4-methoxyphenyl or 1-methyl-1H-pyrazol-3-yl;

when $R^1$ is 4-hydroxyophenyl, $R^3$ is not furan-2-yl;

when $R^1$ is 4-fluorophenyl, $R^3$ is not furan-2-yl or pyridin-4-yl; and when $R^3$ is pyridin-4-yl, $R^1$ is not phenyl, 3-chlorophenyl, 4-hydroxyphenyl or 3-methylphenyl;

or a single stereoisomer, or mixture of stereoisomers, or a pharmaceutically acceptable salt thereof. Preferred in this aspect are those compounds. isomers and salts where:

$R^1$ is optionally substituted aryl or heteroaryl, preferably phenyl, substituted phenyl or pyridinyl (especially 3-chlorophenyl, 4-fluorophenyl, 4-hydroxyphenyl, 3-methylphenyl, pyridin-2-yl or pyridin-3-yl); and $R^3$ is optionally substituted aryl or optionally substituted heteroaryl (especially phenyl, 4-fluorophenyl, 4-cyanophenyl, 4-methoxyphenyl, 4-methylphenyl, isoxazol-5-yl, thiophene-2-yl or 5-methyl-thiophene-2-yl).

Yet other aspects, the invention relates to a pharmaceutical formulation including a pharmaceutically acceptable excipient, and to a method of treatment for heart disease, each entailing a therapeutically effective amount of a compound represented by Formula I, wherein:

$R^1$ is alkyl, substituted alkyl, aryl, substituted aryl, heteroaryl or substituted heteroaryl;

$R^2$ is acetyl, acetylamino, acetylene, alkoxycarbonyl, carboxamido, cyano, halo, heteroaryl, hydrogen, nitrile, nitro or trifluoromethyl; and $R^3$ is aryl, substituted aryl, heteroaryl or substituted heteroaryl;

or a single stereoisomer, or mixture of stereoisomers, or a pharmaceutically acceptable salt thereof. Preferred in this aspect are the above-described preferred compounds, isomers and salts, and those where:

$R^1$ is substituted phenyl (especially 4-fluorophenyl) and $R^2$ is nitro;

$R^1$ is heteroaryl (especially pyridin-3-yl) and $R^2$ is fluoro;

$R^1$ is heteroaryl (especially pyridin-3-yl) and $R^2$ is nitro, particularly where $R^3$ is phenyl, 4-fluorophenyl, 4-cyanophenyl, 4-methoxyphenyl or 4-methylphenyl.

In an additional aspect, the present invention provides methods of screening for compounds that will bind to myosin (particularly myosin III, α cardiac myosin or β cardiac myosin), for example compounds that will displace or compete with the binding of the compounds of the invention. The methods comprise combining a labeled compound of the invention, myosin, and at least one candidate agent and determining the binding of the candidate agent to myosin.

In a further aspect, the invention provides methods of screening for modulators of the activity of myosin. The methods comprise combining a compound of the invention, myosin, and at least one candidate agent and determining the effect of the candidate agent on the activity of myosin.

Other aspects and embodiments will be apparent to those skilled in the art form the following detailed description.

DETAILED DESCRIPTION

DEFINITIONS

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| Boc = | t-butyloxy carbonyl |
| c- = | cyclo |
| CBZ = | carbobenzoxy = benzyloxycarbonyl |
| DOM = | dichloromethane = methylene chloride = $CH_2Cl_2$ |
| DIEA = | N,N-diisopropylethylamine |
| DMF = | N,N-dimethylformamide |
| DMSO = | dimethyl sulfoxide |
| Et = | ethyl |
| EYOAc = | ethyl acetate |
| EtOH = | ethanol |
| GC = | gas chromatograghy |
| h = | hour |
| Me = | methyl |
| min = | minute |
| mL = | milliliter |
| Ph = | phenyl |
| PyBroP = | bromo-tris-pyrrolidinophosphonium hexafluorophosphate |
| rt = | room temperature |
| s- = | secondary |
| t- = | tertiary |
| TFA = | trifluoroacetic acid |
| THF = | tetrahydrofuran |
| TLC = | thin layer chromatography |

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical, synthetically non-feasible and/or inherently unstable.

"Alkyl" is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene is another subset of alkyl, referring to the same residues as alkyl, but having two points of attachment. Examples of alkylene include ethylene ($-CH_2CH_2-$), propylene ($-CH_2CH_2CH_2-$), dimethylpropylene ($-CH_2C(CH_3)_2CH_2-$) and cyclohexylpropylene ($-CH_2CH_2CH(C_6H_{13})-$). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "substituted alkoxy" refers to the group —O-(substituted alkyl). One preferred substituted alkoxy group is "polyalkoxy" or —O-(optionally substituted alkylene)-(optionally substituted alkoxy), and includes groups such as —OCH$_2$CH$_2$OCH$_3$, and glycol ethers such as polyethyleneglycol and —O(CH$_2$CH$_2$O)$_x$CH$_3$, where x is an integer of about 2–20, preferably about 2–10, and more preferably about 2–5. Another preferred substituted alkoxy group is hydroxyalkoxy or —OCH$_2$(CH$_2$)$_y$OH, where y is an integer of about 1–10, preferably about 1–4.

"Acyl" refers to groups of from 1 to 10 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. "Lower-acyl" refers to groups containing 1 to 4 carbons and "acyloxy" refers to the group O-acyl.

The term "amino" refers to the group —NH$_2$. The term "substituted amino" refers to the group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyloxy-sulfonamino.

"Aryl" and "heteroaryl" mean a 5-, 6- or 7-membered aromatic or heteroaromatic ring containing 0–4 heteroatoms selected from O, N or S; a bicyclic 9- or 10-membered aromatic or heteroaromatic ring system containing 0–4 (or more) heteroatoms selected from O, N or S; or a tricyclic 12- to 14-membered aromatic or heteroaromatic ring system containing 0–4 (or more) heteroatoms selected from O, N or S. The aromatic 6- to 14-membered aromatic carbocyclic rings include, e.g., phenyl, naphthalene, indane, tetralin, and fluorene and the 5- to 10-membered aromatic heterocyclic rings include, e.g., imidazole, oxazole, isoxazole, oxadiazole, pyridine, indole, thiophene, benzopyranone, thiazole, furan, benzimidazole, quinoline, isoquinoline, quinoxaline, pyrimidine, pyrazine, tetrazole and pyrazole.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"ATPase" refers to an enzyme that hydrolyzes ATP. ATPases include proteins comprising molecular motors such as the myosins.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, oxadiazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Substituted alkyl, aryl or heteroaryl" refer to alkyl, aryl or heteroaryl, respectively, wherein H atoms are replaced with alkyl, halogen, hydroxy, alkoxy, alkylenedioxy (e.g. methylenedioxy) fluoroalkyl, carboxy (—COOH), carboalkoxy (i.e. acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy. For the purposes of the present invention, substituted alkyl also includes oxaalkyl residues, i.e. alkyl residues in which one or more carbons has been replaced by oxygen.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), —S(O$_2$)-(optionally substituted heterocyclyl), —S(O$_2$)-(optionally substituted alkoxy), —S(O$_2$)-optionally substituted aryloxy), —S(O$_2$)-(optionally substituted heteroaryloxy), and —S(O$_2$)-(optionally substituted heterocyclyloxy).

The term "therapeutically effective amount" or "effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

COMPOUNDS OF THE PRESENT INVENTION

The present invention is directed to the compounds represented by Formula I, which are selective modulators of the cardiac sarcomere (e.g., by stimulating or otherwise potentiating the activity of cardiac myosin), as follows:

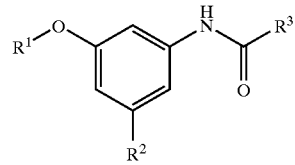

Formula I wherein:

$R^1$ is selected from the group consisting of alkyl, substituted alkyl, aryl, substituted aryl, heteroaryl, and substituted heteroaryl;

$R^2$ is selected from the group: acetyl, acetylamino, acetylene, alkoxycarbonyl, carboxamido, cyano, halo, heteroaryl, hydrogen, nitrile, nitro, and trifluoromethyl; and $R^3$ is selected from the group consisting of aryl, substituted aryl, heteroaryl, and substituted heteroaryl;

including single stereoisomers, mixtures of stereoisomers, and the pharmaceutically acceptable salts thereof. The compounds of Formula I are useful as active agents in practice of the methods of treatment and in manufacture of the pharmaceutical formulations of the invention, and as intermediates in the synthesis of such active agents.

The compounds falling within the foregoing genus and its subgenera are useful as modulators of the cardiac sarcomere. Some of the compounds were obtained from commercially available compound libraries. The provisos in the claims are meant to distinguish between subject matter that is patentable as a composition of matter vs. subject matter that can be claimed based on applicants' recognition of its therapeutic/pharmaceutical utility.

NOMENCLATURE

The compounds of Formula I can be named and numbered (e.g., using AutoNom version 2.1) as described below. For example, the compound of Formula IA:

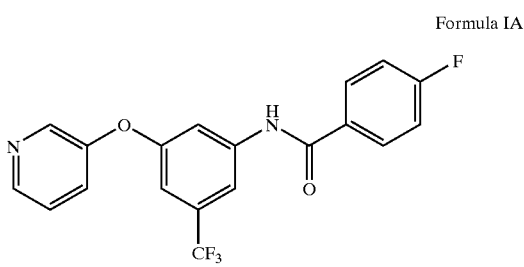

Formula IA i.e., the compound according to Formula I where $R^1$ is pyridin-3-yl, $R^2$ is trifluoromethyl and $R^3$ is 4-fluorophenyl, can be named 4-fluoro-N-[3-(pyridin-3-yloxy)-5-trifluoromethyl-phenyl]-benzamide.

The compound of Formula IB:

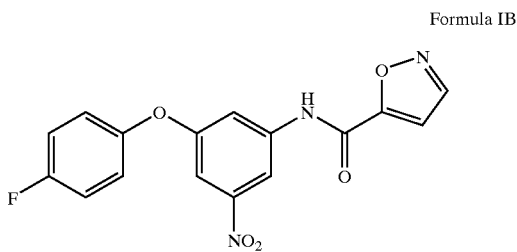

Formula IB i.e., the compound according to Formula I where $R^1$ is 4-fluorophenyl, $R^2$ is nitro and $R^3$ is isoxalyl-5-yl, can be named isoxazole-5-carboxylic acid [3-(4-fluoro-phenoxy)-5-nitro-phenyl-amide.

SYNTHESIS OF THE COMPOUNDS OF FORMULA I

The compounds of the invention can be synthesized utilizing techniques well known in the art. See, for example, Zlotin et al. (2000) J. Org. Chem. 65(25), 8430–8438; Shkinyova et al. (2000) Tetrahedron Letters 41(25), 4973–4975; Shevelev et al. (1995) Mendeleev Commun. (1995), (4), 157–8; Kamifuji et al. (1993) Jpn. Kokai Tokkyo Koho JP 05043556; and Cui (2001) German Patent Appln. No. 2000-10010002, each of which is incorporated by reference.

Syntheses of the compounds of Formula I are illustrated below with reference to Reaction Scheme 1.

SYNTHETIC REACTION PARAMETERS

Unless specified to the contrary, the reactions described herein take place at atmospheric pressure, generally within a temperature range from −10° C. to 110° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)- and (S)-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

BRIEF DESCRIPTION OF REACTION SCHEME

Reaction Scheme 1 illustrates synthesis of the compounds of Formula I, starting from a substituted nitro-benzene, which is condensed with an $R^1$ alcohol, optionally derivatized to introduce the $R^2$ substituent, reduced to the corresponding amino-benzene and acidified to afford Formula I.

It will be appreciated by those skilled in the art that one or more of the reactants, steps and/or conditions described with reference to Reaction Scheme 1 may require adjustment to accommodate various substituents, e.g., at $R^1$ to $R^3$.

STARTING MATERIALS

The nitro-benzenes of Formula 101 (e.g., 3-fluoro-5-iodo-nitro-benzene and 3,5-difluoro-nitro-benzene), the $R^1$-alcohols of Formula 102 (e.g., 4-fluoro-phenol and pyridin-3-ol) and the like are commercially available, e.g., from Aldrich Chemical Company, Milwaukee, Wis. Other reactants are likewise commercially available or may be readily prepared by those skilled in the art using commonly employed synthetic methodology.

REACTION SCHEME 1

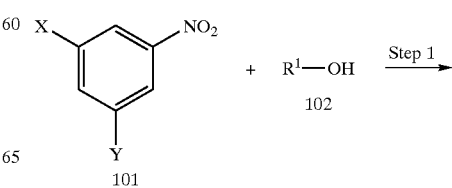

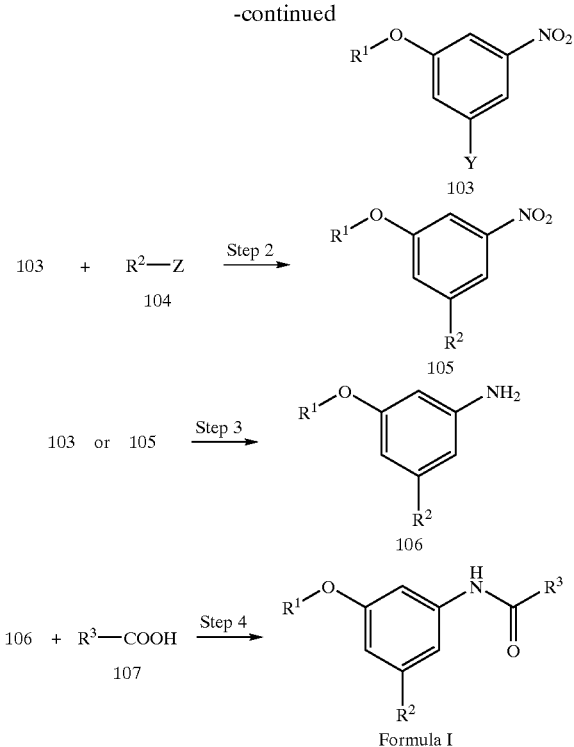

Preparation of Formula 103 Referring to Reaction Scheme 1, Step 1, a nitro-benzene of Formula 101 (where X is F or $NO_2$, and Y is acetyl, acetylamino, $CF_3$, $C(O)CH_3$, C(O)O-alkyl, CN, H, halo, $NO_2$, or the like) and an alkyl-, aryl- or heteroaryl-alcohol of Formula 102 are contacted in a solvent (e.g., DMF) in the presence of a base (e.g., $K_2CO_3$). The solution is stirred for 1–96 hours at room temperature to 150° C. to afford the corresponding alkoxy-, aryloxy- or heteroaryloxy-nitro-benzene of Formula 103, which is conventionally isolated and purified. The compound of Formula 103 can be carried forward to Reaction Scheme 1, Step 2 or directly to Reaction Scheme 1, Step 3.

Preparation of Formula 105 Referring to Reaction Scheme 1, Step 2, conversion of the alkoxy-, aryloxy- or heteroaryloxy-nitro-benzene of Formula 103 to the corresponding $R^2$-Substituted nitro-benzene of Formula 105 takes place with a variety of reactants (generically illustrated as Formula 104) and conditions depending on the nature of $R^2$, for example, as follows:

Where $R^2$ is acetylene, a compound of Formula 103, wherein Y is I or Br, is contacted with palladium (e.g., PdOAc) and copper (e.g., CuI) catalysts, a base (e.g., diethylamine) and trimethylsilylacetylene of Formula 104, followed by removal of the trimethylsilyl with a fluoride source (e.g., tetrabutylammonium fluoride "TBAF"). The reaction takes place over 1–48 hours at room temperature to 150° C., or for 1–30 min. with microwave irradiation, to afford the corresponding acetylene-substituted nitro-benzene of Formula 105. Alternatively, this reaction can be run on a compound of Formula I where $R^2$ is I or Br (e.g., where a compound of Formula 103 is carried forward directly to Reaction Scheme 1, Step 3).

Where $R^2$ is heteroaryl, a compound of Formula 103 wherein Y is I or Br, is contacted with a heteroaryl organometalic (e.g., an organozinc, an organoboronic acid, or an organotin) of Formula 104 in the presence of a palladium catalyst. The reaction takes place over 1–48 hours at room temperature to 150° C., or for 1–30 min. with microwave irradiation, to afford the corresponding heteroaryl-substituted nitro-benzene of Formula 105. Alternatetively, this reaction can be run on a compound of Formula I where $R^2$ is I or Br (e.g., where a compound of Formula 103 is carried forward directly to Reaction Scheme 1, Step 3).

The $R^2$-Substituted nitro-benzene of Formula 105 can be conventionally isolated and purified, or carried forward without isolation and purification.

Preparation of Formula 106 Referring to Reaction Scheme 1, Step 3, a nitro-benzene of Formula 105 is reduced under typical conditions (e.g., Pd/C with $H^2$, $NH_4COOH$ or Zn/HCl or $SnCl_2$). The solution is stirred for 1–48 hours at room temperature to 150° C. to afford the corresponding amino-benzene of Formula 106, which is conventionally isolated and purified.

Preparation of Formula I Referring to Reaction Scheme 1, Step 4, an amino-benzene of Formula 106 is contacted with an aryl- or heteroaryl-acid or acid chloride of Formula 107 under standard amide coupling conditions that readily assessable by those skilled in the art using commonly employed synthetic methodology to afford the corresponding compound of Formula I, which is conventionally isolated and purified.

Compounds prepared by the above-described process of the invention can be identified, e.g., by the presence of a detectable amount of Formula 106 or 107. While it is well known that pharmaceuticals must meet pharmacopoeia standards before approval and/or marketing, and that synthetic reagents (such as 4-fluoro-benzoic acid) and precursors (such as Formula 106) should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a synthetic process of the invention.

PREFERRED PROCESSES AND LAST STEPS

A substituted amino-benzene compound of Formula 106 is condensed with an aryl- or heteroaryl-acid or acid chloride of Formula 107 to afford the corresponding compound of Formula I.

A racemic mixture of isomers of a compound of Formula I is placed on a chromatography column and separated into (R)- and (S)-enantiomers.

A compound of Formula I is contacted with a pharmaceutically acceptable acid to form the corresponding acid addition salt.

A pharmaceutically acceptable acid addition salt of Formula I is contacted with a base to form the corresponding free base of Formula I.

PREFERRED COMPOUNDS

Preferred for the compounds, pharmaceutical formulations, methods of manufacture and use of the present invention are the following combinations and permutations of substituent groups of Formula I (sub-grouped, respectively, in increasing order of preference):

$R^1$ is optionally substituted aryl or heteroaryl.
  Especially where optionally substituted aryl is phenyl or substituted phenyl, and/or where heteroaryl is pyridinyl.

Particularly pyridin-2-yl or pyridin-3-yl.
Preferably, $R^1$ is pyridin-3-yl and $R^2$ is fluoro.
Particularly phenyl optionally substituted with lower alkyl, halo or hydroxy.
Preferably 3-chlorophenyl, 4-fluorophenyl, 4-hydroxyphenyl and 3-methylphenyl.
More preferably 4-fluorophenyl.
Even more preferably, $R^1$ is 4-fluorophenyl and $R^2$ is nitro.
Most preferably, $R^1$ is pyridin-2-yl, pyridin-3-yl or 4-fluorophenyl.
$R^2$ is acetyl, acetylene, an alkyl ester, cyano, halo, optionally substituted heteroaryl, hydrogen, nitro (subject to the provisos identified above and in the claims) or trifluoromethyl.
Especially where halo is fluoro; where the alkyl ester is ethoxycarbonyl; and/or where heteroaryl is oxazolyl, pyrazinyl, pyridinyl, pyrimidinyl, tetrazolyl or thiazolyl, optionally substituted with lower alkoxy or oxo.
Particularly where optionally substituted heteroaryl is oxazol-2-yl, pyrazin-2-yl, pyridin-1-yl (particularly 3-methoxy-2-oxo-2H-pyridin-1-yl), pyridin-2-yl, pyrimidin-2-yl, tetrazol-2-yl (particularly 1-methoxymethoxy-1H-tetrazol-5-yl, 2-methoxymethoxy-2H-tetrazol-5-yl) or thiazol-2-yl.
Most preferably $R^2$ is acetylene, cyano, ethoxycarbonyl, fluoro, hydrogen, nitro, oxazol-2-yl, pyridin-2-yl, pyrimidin-2-yl, thiazol-2-yl or trifluoromethyl.
$R^3$ is optionally substituted aryl or optionally substituted heteroaryl.
Especially when $R^3$ is optionally substituted aryl, where aryl is phenyl, optionally substituted with lower alkoxy, lower alkyl, halo (particularly bromo, chloro or fluoro), hydroxy, hydroxy-lower alkyl or nitro.
Particularly 3-bromophenyl, 4-chlorophenyl, 4-cyanophenyl, 3-fluorophenyl, 4-fluorophenyl, 3-hydroxyphenyl, 4-hydroxyethylphenyl, 4-hydroxyphenyl, 3-methylphenyl, 4-methoxyphenyl, 3,4,5-trimethoxyphenyl, or 4-nitrophenyl.
Especially when $R^3$ is optionally substituted heteroaryl, where heteroaryl is benzodioxolyl, furanyl, indolyl, isoxazolyl, pyrazolyl, pyridinyl or thiophenyl, optionally substituted with lower alkyl, lower alkoxy, or halo.
Particularly benzo[1,3]dioxol-5-yl, furan-2-yl, 5-fluoro-1H-indol-2-yl, 5-methoxy-1H-indol-2-yl, 6-methoxy-1H-indol-2-yl, isoxazol-5-yl, 1-methyl-1H-pyrazol-3-yl, 6-chloro-pyridin-3-yl, 5,6-dichloro-pyridin-3-yl, 6-methoxy-pyridin-3-yl, pyridin-4-yl, thiophen-2-yl, 5-chlorothiophen-2-yl, or 5-methylthiophen-2-yl.
Especially where $R^3$ is substituted aryl or optionally substituted heteroaryl.
Particularly substituted phenyl or optionally substituted isoxazolyl, pyridinyl, or thiophenyl.
Preferably 3-hydroxyphenyl, 4-hydroxyphenyl, 4-fluorophenyl, isoxazol-5-yl, pyridin-3-yl, pyridin-4-yl, thiophen-2-yl or 5-methyl-thiophen-2-yl.
More preferably 4-fluorophenyl.
Most preferably where $R^1$ is pyridin-3-yl.
Particularly where $R^1$ is optionally substituted aryl or heteroaryl.
Preferably where optionally substituted aryl is phenyl or substituted phenyl, and/or where heteroaryl is pyridinyl.
More preferably pyridin-2-yl or pyridin-3-yl.
More preferably phenyl optionally substituted with lower alkyl, halo or hydroxy.
Even more preferably 3-chlorophenyl, 4-fluorophenyl, 4-hydroxyphenyl and 3-methylphenyl.
Still more preferably 4-fluorophenyl.
Most preferably, $R^1$ is pyridin-2-yl, pyridin-3-yl or 4-fluorophenyl.
Particularly where $R^2$ is acetyl, acetylene, an alkyl ester, cyano, halo, optionally substituted heteroaryl, hydrogen, nitro or trifluoromethyl.
Preferably where halo is fluoro; where the alkyl ester is ethoxycarbonyl; and/or where heteroaryl is oxazolyl, pyrazinyl, pyridinyl, pyrimidinyl, tetrazolyl or thiazolyl, optionally substituted with lower alkoxy or oxo.
More preferably where optionally substituted heteroaryl is oxazol-2-yl, pyrazin-2-yl, pyridin-1-yl (particularly 3-methoxy-2-oxo-2H-pyridin-1-yl), pyridin-2-yl, pyrimidin-2-yl, tetrazol-2-yl (particularly 1-methoxymethoxy-1H-tetrazol-5-yl, 2-methoxymethoxy-2H-tetrazol-5-yl) or thiazol-2-yl.
Most preferably $R^2$ is acetylene, cyano, ethoxycarbonyl, fluoro, hydrogen, nitro, oxazol-2-yl, pyridin-2-yl, pyrimidin-2-yl, thiazol-2-yl or trifluoromethyl.
Especially where $R^1$ is optionally substituted aryl or heteroaryl.
Particularly where optionally substituted aryl is phenyl or substituted phenyl, and/or where heteroaryl is pyridinyl.
Preferably pyridin-2-yl or pyridin-3-yl.
Preferably phenyl optionally substituted with lower alkyl, halo or hydroxy.
More preferably 3-chlorophenyl, 4-fluorophenyl, 4-hydroxyphenyl and 3-methylphenyl.
Even more preferably 4-fluorophenyl.
Most preferably, $R^1$ is pyridin-2-yl, pyridin-3-yl or 4-fluorophenyl.
Particularly where $R^2$ is acetyl, acetylene, an alkyl ester, cyano, halo, optionally substituted heteroaryl, hydrogen, nitro or trifluoromethyl.
Preferably where halo is fluoro; where the alkyl ester is ethoxycarbonyl; and/or where heteroaryl is oxazolyl, pyrazinyl, pyridinyl, pyrimidinyl, tetrazolyl or thiazolyl, optionally substituted with lower alkoxy or oxo.
More preferably where optionally substituted heteroaryl is oxazol-2-yl, pyrazin-2-yl, pyridin-1-yl (particularly 3-methoxy-2-oxo-2H-pyridin-1-yl), pyridin-2-yl, pyrimidin-2-yl, tetrazol-2-yl (particularly 1-methoxymethoxy-1H-tetrazol-5-yl, 2-methoxymethoxy-2H-tetrazol-5-yl) or thiazol-2-yl.
Most preferably $R^2$ is acetylene, cyano, ethoxycarbonyl, fluoro, hydrogen, nitro, oxazol-2-yl, pyridin-2-yl, pyrimidin-2-yl, thiazol-2-yl or trifluoromethyl.
Especially where $R^2$ is acetyl, acetylene, an alkyl ester, cyano, halo, optionally substituted heteroaryl, hydrogen, nitro or trifluoromethyl.
Particularly where halo is fluoro; where the alkyl ester is ethoxycarbonyl; and/or where heteroaryl is oxazolyl, pyrazinyl, pyridinyl, pyrimidinyl, tetrazolyl or thiazolyl, optionally substituted with lower alkoxy or oxo.

Preferably where optionally substituted heteroaryl is oxazol-2-yl, pyrazin-2-yl, pyridin-1-yl (particularly 3-methoxy-2-oxo-2H-pyridin-1-yl), pyridin-2-yl, pyrimidin-2-yl, tetrazol-2-yl (particularly 1-methoxymethoxy-1H-tetrazol-5-yl, 2-methoxymethoxy-2H-tetrazol-5-yl) or thiazol-2-yl.

More preferably $R^2$ is acetylene, cyano, ethoxycarbonyl, fluoro, hydrogen, nitro, oxazol-2-yl, pyridin-2-yl, pyrimidin-2-yl, thiazol-2-yl or trifluoromethyl.

$R^1$ is heteroaryl and $R^3$ is substituted phenyl.

Especially where $R^1$ is pyridin-3-yl.

Particularly where $R^2$ is acetylene, cyano, ethoxycarbonyl, fluoro, hydrogen, nitro, oxazol-2-yl, pyridin-2-yl, pyrazin-2-yl, thiazol-2-yl or trifluoromethyl.

Preferably where $R^2$ is nitro or fluoro.

Preferably where $R^3$ is 4-fluorophenyl.

Particularly, as novel compositions of matter, where $R^2$ is cyano, ethoxycarbonyl, hydrogen, fluoro, hydrogen, pyridin-2-yl, pyrazin-2-yl, or trifluoromethyl.

Especially where $R^3$ is 4-fluorophenyl.

Preferably where $R^1$ is pyridin-3-yl.

$R^1$ is substituted phenyl and $R^2$ is nitro.

Especially where $R^1$ is 4-fluorophenyl.

$R^1$ is heteroaryl and $R^2$ is fluoro.

Especially where $R^1$ is pyridin-3-yl.

$R^1$ is heteroaryl and $R^2$ is nitro.

Especially where $R^1$ is pyridin-3-yl.

Particularly where $R^3$ is optionally substituted aryl.

Preferably where $R^3$ is phenyl, 4-fluorophenyl, 4-cyanophenyl, 4-methoxyphenyl or 4-methylphenyl.

As illustrated with regard to the group of preferred compounds where $R^3$ is optionally substituted aryl, optionally substituted heteroaryl or optionally substituted heteroarylamino, the above-described groups and subgroups are individually preferred and can be combined to describe further preferred aspects of the invention.

Particularly preferred (individually and collectively) for the pharmaceutical formulations, methods of manufacture and use of the present invention are the following:

4-fluoro-N-[nitro-5-(pyidin-3-yloxy)-phenyl]-benzamide;
N-[3-(4-fluoro-phenoxy)-(5-nitro-phenyl]-isonicotinamide;
4-fluoro-N-[3-(pyridin-3-yloxy)-phenyl]-benzamide;
thiophene-2-carboxylic acid [3-(4-fluoro-phenoxy)-5-nitro-phenyl-amide;
isoxazole-5-carboxylic acid [3-(4-fluoro-phenoxy)-5-nitro-phenyl-amide;
N-[3-cyano-5-(pyridin-3-yloxy)-phenyl]]-4-fluoro-benzamide;
4-fluoro-N-[3-(pyridin-3-yloxy)-5-trifluoromethyl-phenyl]-benzamide;
3-(4-fluoro-benzoylamino)-5-(pyridin-3-yloxy)-benzoic acid ethyl ester;
5-methyl-thiophene-2-carboxylic acid [3-nitro-5-(pyridin-3-yloxy)phenyl]-amide;
4-fluoro-N-[3-pyridin-2-yl-5-(pyridin-3-yloxy)-phenyl]-benzamide;
4-fluoro-N-[3-pyrazin-2-yl-5-(pyridin-3-yloxy)-phenyl]-benzamide;
4-fluoro-N-[3-nitro-5-(pyridin-2-yloxy)-phenyl]-benzamide;
N-[3-fluoro-5-(pyridin-3-yloxy)-phenyl]-3-hydroxy-benzamide;
N-[3-fluoro-5-(pyridin-3-yloxy)-phenyl]-4-hydroxy-benzamide;
N-[3-fluoro-5-(pyridin-3-yloxy)-phenyl]-nicotinamide; and
isoxazole-5-carboxylic acid [3-fluoro-5-(pyridin-3-yloxy)-phenyl)-amide.

More preferred (individually and collectively) as novel compounds of the present invention, including their formulations, methods of manufacture and use, are the following:

4-fluoro-N-[3-(pyridin-3-yloxy)-phenyl]-benzamide;
thiophene-2-carboxylic acid [3-(4-fluoro-phenoxy)-5-nitro-phenyl-amide;
isoxazole-5-carboxylic acid [3-(4-fluoro-phenoxy)-5-nitro-phenyl-amide;
N-[3-cyano-5-(pyridin-3-yloxy)-phenyl]]-4-fluoro-benzamide;
4-fluoro-N-[3-(pyridin-3-yloxy)-5-trifluoromethyl-phenyl]-benzamide;
3-(4-fluoro-benzoylamino)-5-(pyridin-3-yloxy)-benzoic acid ethyl ester;
5-methyl-thiophene-2-carboxylic acid [3-nitro-5-(pyridin-3-yloxy)phenyl]-amide;
4-fluoro-N-[3-pyridin-2-yl-5-(pyridin-3-yloxy)-phenyl]-benzamide;
4-fluoro-N-[3-pyrazin-2-yl-5-(pyridin-3-yloxy)-phenyl]-benzamide;
4-fluoro-N-[3-nitro-5-(pyridin-2-yloxy)-phenyl]-benzamide;
N-[3-fluoro-5-(pyridin-3-yloxy)-phenyl]-3-hydroxy-benzamide;
N-[3-fluoro-5-(pyridin-3-yloxy)-phenyl]-4-hydroxy-benzamide;
N-[3-fluoro-5-(pyridin-3-yloxy)-phenyl]-nicotinamide; and
isoxazole-5-carboxylic acid [3-fluoro-5-(pyridin-3-yloxy)-phenyl)-amide.

UTILITY, TESTING AND ADMINISTRATION

UTILITY

The compounds of the present invention are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative compounds of the invention, that their administration can also increase the contractile force in cardiac muscle fiber.

The compounds, pharmaceutical formulations and methods of the invention are used to treat heart disease, including but not limited to: acute (or decompensated) congestive heart failure, and chronic congestive heart failure; particularly diseases associated with systolic heart dysfunction. Additional therapeutic utilities include administration to stabilize heart function in patients awaiting a heart transplant, and to assist a stopped or slowed heart in resuming normal function following use of a bypass pump.

TESTING

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A compound that modulates the cardiac sarcomere can be identified by an increase or decrease in the rate of ATP hydrolysis by myosin, preferably exhibiting a 1.4 fold increase at concentrations less than 10 $\mu$M (more preferably, less than 1 $\mu$M). Preferred assays for such activity will employ myosin from a human source, although myosin from other organisms can also be used. Systems that model the regulatory role of calcium in myosin binding are also preferred.

Alternatively, a biochemically functional sarcomere preparation can be used to determine in vitro ATPase activity, for example, as described in U.S. Ser. No. 09/539, 164, filed Mar. 29, 2000 (now U.S. Pat. No. 6,410,245). The functional biochemical behavior of the sarcomere, including calcium sensitivity of ATPase hydrolysis, can be reconstituted by combining its purified individual components (particularly including its regulatory components and myosin). Another functional preparation is the in vitro motility assay. It can be performed by adding test compound to a myosin-bound slide and observing the velocity of actin filaments sliding over the myosin covered glass surface (Kron S J. (1991) Methods Enzymol. 196:399–416).

The in vitro rate of ATP hydrolysis correlates to myosin potentiating activity, which can be determined by monitoring the production of either ADP or phosphate, for example as described in Ser. No. 09/314,464, filed May 18, 1999 (now U.S. Pat. No. 6,495,337). ADP production can also be monitored by coupling the ADP production to NADH oxidation (using the enzymes pyruvate kinase and lactate dehydrogenase) and monitoring the NADH level either by absorbance or fluorescence (Greengard, P., Nature 178 (Part 4534): 632–634 (1956); Mol Pharmacol 1970 January;6(1):31–40). Phosphate production can be monitored using purine nucleoside phosphorylase to couple phosphate production to the cleavage of a purine analog, which results in either a change in absorbance (Proc Natl Acad Sci USA 1992 Jun. 1;89(11):4884–7) or fluorescence (Biochem J 1990 Mar. 1;266(2):611–4). While a single measurement can be employed, it is preferred to take multiple measurements of the same sample at different times in order to determine the absolute rate of the protein activity; such measurements have higher specificity particularly in the presence of test compounds that have similar absorbance or fluorescence properties with those of the enzymatic readout.

Test compounds can be assayed in a highly parallel fashion using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

A preferred method uses a 384 well plate format and a 25 $\mu$L reaction volume. A pyruvate kinase/lactate dehydrogenase coupled enzyme system (Huang T G and Hackney D D. (1994) J Biol Chem 269(23):16493–16501) is used to measure the rate of ATP hydrolysis in each well. As will be appreciated by those in the art, the assay components are added in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber contractile force can be measured using detergent permeabilized cardiac fibers (also referred to as skinned cardiac fibers), for example, as described by Haikala H, et al (1995) J Cardiovasc Pharmacol 25(5):794–801. Skinned cardiac fibers retain their intrinsic sarcomeric organization, but do not retain all aspects of cellular calcium cycling, this model offers two advantages: first, the cellular membrane is not a barrier to compound penetration, and second, calcium concentration is controlled. Therefore, any increase in contractile force is a direct measure of the test compound's effect on sarcomeric proteins. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the permeabilized muscle fiber is accomplished by placing it in a buffered calcium solution, followed by addition of test compound or control. When tested in this manner, compounds of the invention caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

Initial evaluation of in vivo activity can be determined in cellular models of myocyte contractility, e.g., as described by Popping S, et al ((1996) Am. J. Physiol. 271: H357–H364) and Wolska B M, et al ((1996) Am. J. Physiol. 39:H24–H32). One advantage of the myocyte model is that the component systems that result in changes in contractility can be isolated and the major site(s) of action determined. Compounds with cellular activity (for example, selecting compounds having the following profile: >120% increase in fractional shortening over basal at 2 $\mu$M, limited changes in diastolic length (<5% change), and no significant decrease in contraction or relaxation velocities) can then be assessed in whole organ models, such as such as the Isolated Heart (Langendorff) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

ADMINISTRATION

The compounds of Formula I are administered at a therapeutically effective dosage, e.g., a dosage sufficient to provide treatment for the disease states previously described. While human dosage levels have yet to be optimized for the compounds of the invention, generally, a daily dose is from about 0.05 to 100 mg/kg of body weight, preferably about 0.10 to 10.0 mg/kg of body weight, and most preferably about 0.15 to 1.0 mg/kg of body weight. Thus, for administration to a 70 kg person, the dosage range would be about 3.5 to 7000 mg per day, preferably about 7.0 to 700.0 mg per day, and most preferably about 10.0 to 100.0 mg per day. The amount of active compound administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 700 to 7000 mg per day, the active agents being selected for longer or shorter plasma half-lives, respectively.

Administration of the compounds of the invention or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The compounds can also be administered in sustained or controlled release dosage forms, including depot injections, osmotic pumps, pills, transdermal (including electrotransport) patches, and the like, for prolonged and/or timed, pulsed administration at a predetermined rate. Preferably, the compositions are provided in unit dosage forms suitable for single administration of a precise dose.

The compounds can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see *Remington's Pharmaceutical Sciences*, Mack Publishing Company, Easton, Pa.

In addition, the compounds of the invention can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or β-blockers); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide).

In one preferred embodiment, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

USE IN SCREENING

Generally, to employ the compounds of the invention in a method of screening for myosin binding, myosin is bound to a support and a compound of the invention is added to the assay. Alternatively, the compound of the invention can be bound to the support and the myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

N-[3-Cyano-5-(pyridin-3-yloxy)-phenyl]]-4-fluoro-benzamide

1A. Formula 103 where $R^1$ is Pyridin-3-yl and Y is CN

A solution of 1 equivalent (eq., 25.42 g, 131.6 mmol)) of 1,3 dinitro-5-cyanobenzene in 1.75 M DMF (75 mL), 1 eq. 3-hydroxypyridine (12.52 g, 131.6 mmol) and 2 eq. potassium carbonate (36.38 g, 263 mmol) was heated to 60° C. overnight. The reaction mixture was warmed to 95° C. for an additional 48 hours. The reaction mixture was diluted with EtOAc, washed with $H_2O$, sat. $NaHCO_3$, and brine, dried over $Na_2SO_4$ and concentrated in vacuo. Purification by chromatography over silica with 25% EtOAC/Hexane as the eluant afforded 10.04 g of the desired compound of Formula 103, 3-(pyridin-3-yloxy)-5-cyano-1-nitrobenzene, as a solid (32% yield).

1B. Formula 106 where $R^1$ is Pyridin-3-yl and $R^2$ is CN

To a solution of 1 eq. (5.5 g, 22.8 mmol) of 3-(pyridin-3-yloxy)-5-cyano-1-nitrobenzene 0.23 M in EtOH (100 mL) was added 3 eq. of tin (II) chloride (15.5 g, 68 mmol) and the resultant mixture stirred under a nitrogen atmosphere at rt overnight. The reaction mixture was diluted with water (100 mL) and the pH adjusted to 9 by the addition of saturated Na$_2$CO$_3$. The mixture was extracted with EtOAc (3 times), the combined organic layers dried (Na$_2$SO$_4$) and conc. in vacuo. Purification by chromatography over silica with 2% MeOH/CH$_2$Cl$_2$ as the eluant afforded 1.09 g of the desired compound of Formula 103, 3-(pyridin-3-yloxy)-5-cyano-aniline, as a solid (23% yield).

1C. Formula I where R$^1$ is Pyridin-3-yl, R$^2$ is CN, and R$^3$ is 4-Fluorophenyl To a solution of 1 eq. (0.1 g, 0.473 mmol) of 3-(pyridin-3-yloxy)-5-cyano-aniline in 0.47 M in CH$_2$Cl$_2$ (1 mL) and 1.6 eq. of pyridine (0.56 g, 0.71 mmol) was added 3 eq. of 4-fluorobenzoyl chloride (0.225 g, 1.42 mmol) and the resultant mixture stirred at rt overnight. The reaction mixture was diluted with CH$_2$Cl$_2$, washed with sat. NaHCO$_3$, dried (Na$_2$SO$_4$) and concentrated in vacuo. The resultant residue was diluted with toluene and concentrated in vacuo (5 times). Purification by chromatography over silica with 5% MeOH/CH$_2$Cl$_2$ as the eluant afforded 134 mg of a the desired title compound of Formula I, N-[3-cyano-5-(pyridin-3-yloxy)-phenyl]]-4-fluoro-benzamide, as a solid (85% yield). Mpt 169–172° C. MS (M−1) 332.3.

Example 2

4-Fluoro-N-[3-pyridin-2-yl-5-(pyridin-3-yloxy)-phenyl]-benzamide

2A. Formula I where R$^1$ is Pyridin-3-yl, R$^2$ is Pyridin-2-yl, and R$^3$ is 4-Fluorophenyl A mixture of 1 eq. (175 mg, 0.402 mmol) of 4-fluoro-N-[3-iodo-5-(pyridin-3-yloxy)-phenyl]-benzamide 1.15 eq. (170 mg, 0.463 mmol) of 2-tributyltinpyridine, and 0.04 eq. (11 mg, 0.10 mmol) of bis-(triphenylphosphine)dichloropalladium in 2 mL of THF was irradiated for in a microwave for 10 minutes an 170° C. The reaction mixture was filtered and concentrated in vacuo. Purification by chromatography over silica with 50% EtOAC/Hexane to 75% EtOAc/Hexane as the gradient eluant afforded 30 mg of a solid (4-fluoro-N-[3-pyridin-2-yl-5-(pyridin-3-yloxy)-phenyl]-benzamide, (19% yield). Mpt 160–162° C. MS (M+1) 386.1.

Example 3

Other Compounds of Formula I

Similarly, by following the procedures of Examples 1 and/or 2, and e.g., substituting the 1,3 dinitro-5-cyanobenzene, 3-hydroxypyridine, 4-fluorobenzoyl chloride and/or 2-tributyltinpyridine as described in connection with Reaction Scheme 1, there were obtained:
4-fluoro-N-[nitro-5-(pyidin-3-yloxy)-phenyl]-benzamide, MS (M+1) 354.2;
N-[3-(4-fluoro-phenoxy)-(5-nitro-phenyl]-isonicotinamide, MS (M−1) 352.3;
4-fluoro-N-[3-(pyridin-3-yloxy)-phenyl]-benzamide, MS (M+1) 309.4;
thiophene-2-carboxylic acid [3-(4-fluoro-phenoxy)-5-nitro-phenyl-amide, MS (M−1) 356.6;
isoxazole-5-carboxylic acid [3-(4-fluoro-phenoxy)-5-nitro-phenyl-amide, MS (M−1) 341.6;
4-fluoro-N-[3-(pyridin-3-yloxy)-5-trifluoromethyl-phenyl]-benzamide, MS (M+1) 377.2;
3-(4-fluoro-benzoylamino)-5-(pyridin-3-yloxy)-benzoic acid ethyl ester, MS (M+1) 381.2;
5-methyl-thiophene-2-carboxylic acid [3-nitro-5-(pyridin-3-yloxy)phenyl]-amide, MS (M−1) 353.9;
4-fluoro-N-[3-pyrazin-2-yl-5-(pyridin-3-yloxy)-phenyl]-benzamide, MS (M−1) 385.4;
4-fluoro-N-[3-nitro-5-(pyridin-2-yloxy)-phenyl]-benzamide, MS (M+1) 354.2;
N-[3-fluoro-5-(pyridin-3-yloxy)-phenyl]-3-hydroxy-benzamide, MS (M+1) 325.1;
N-[3-fluoro-5-(pyridin-3-yloxy)-phenyl]-4-hydroxy-benzamide, MS (M+1) 325.2;
N-[3-fluoro-5-(pyridin-3-yloxy)-phenyl]-nicotinamide, MS (M+1) 310.1;
isoxazole-5-carboxylic acid [3-fluoro-5-(pyridin-3-yloxy)-phenyl)-amide, MS (M+1) 300.1;
5,6-dichloro-N-[3-nitro-5-(pyridin-3-yloxy)-phenyl]-nicotinamide, MS (M−1) 402.3;
4-fluoro-N-[3-[1-(2-methoxy-ethoxymethyl)-1H-tetrazol-5-yl]-5-(pyridin-3-yloxy)-phenyl]-benzamide, MS (M+1) 465.3;
3-(4-fluoro-benzoylamino)-5-(pyridin-3-yloxy)-benzenesulfonic acid pyridin-3-yl ester, MS (M+1) 466.1;
6-methoxy-1H-indole-2-carboxylic acid [3-fluoro-5-(pyridin-3-yloxy)-phenyl]-amide, MS (M+1) 378.1; and
1-[3-(3-methoxy-2-oxo-2H-pyridin-1-yl)-5-(pyridin-3-yloxy)-phenyl]-3-(6-methoxy pyridin-3-yl)-urea, MS (M+1) 459.2.

Example 4

In Vitro Model of Dose Dependent Cardiac Myosin ATPase Modulation

Dose responses are measured using a calcium-buffered, pyruvate kinase and lactate dehydrogenase-coupled ATPase assay containing the following reagents (concentrations expressed are final assay concentrations): Potassium PIPES (12 mM), MgCl$_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 $\mu$M), bovine cardiac actin (14 $\mu$M), bovine cardiac tropomyosin (typically 3 $\mu$M), and bovine cardiac troponin (typically 3–8 $\mu$M). The exact concentrations of tropomyosin and troponin are determined empirically, by titration to achieve maximal difference in ATPase activity when measured in the presence of 1 mM EGTA versus that measured in the presence of 0.2 mM CaCl$_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration, corresponding to 50% of maximal ATPase activity (pCa$_{50}$), so a preliminary experiment is performed to test the response of the ATPase activity to free calcium concentrations in the range of $1 \times 10^{-4}$ M to $1 \times 10^{-8}$ M. Subsequently, the assay mixture is adjusted to the pCa$_{50}$ (typically $3 \times 10^{-7}$ M). Assays are performed by first preparing a dilution series of test compound, each with an assay mixture containing potassium Pipes, MgCl$_2$, BSA, DTT, pyruvate kinase, lactate dehydrogenase, myosin subfragment-1, antifoam, EGTA, CaCl$_2$, and water. The assay is started by adding an equal volume of solution containing potassium Pipes, MgCl$_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top−Bottom)/(1+((EC50/

X)^Hill))). The AC1.4 is defined as the concentration at which ATPase activity is 1.4-fold higher than the bottom of the dose curve.

Preferred compounds of the invention have an AC1.4 less than 10 μM; and more preferably, less than 1 μM.

When tested as described above, compounds of Formula I show activity as potentiators of cardiac myosin.

Example 5

Myocyte Calcium-Contractility Assay

5A. PREPARATIONS OF ADULT CARDIAC VENTRICULAR RAT MYOCYTES

Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm $H_2O$. Hearts are first perfused with a nominally $Ca^{2+}$ free modified Krebs solution of the following composition: 110 mM NaCl, 2.6 mM KCL, 1.2 mM $KH_2PO_4$ $7H_2O$, 1.2 mM $MgSO_4$, 2.1 mM $NaHCO_3$, 11 mM glucose and 4 mM Hepes (all Sigma). This medium is not recirculated and is continually gassed with $O_2$. After approximately 3 minutes the heart is perfused with modified Krebs buffer supplemented with 3.3% collagenase (169 μ/mg activity, Class II, Worthington Biochemical Corp., Freehold, N.J.) and 25 μM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 μm nylon mesh in a 50 cc tube. The resulting myocytes are resuspended in modified Krebs solution containing 25 μm calcium. Myocytes are made calcium tolerant by addition of a calcium solution (100 mM stock) at 10 minute intervals until 100 μM calcium is achieved. After 30 minutes the supernatant is discarded and 30–50 ml of Tyrode buffer (137 mM NaCL, 3.7 mM KCL, 0.5 mM MgCL, 11 mM glucose, 4 mM Hepes, and 1.2 mM $CaCl_2$, pH 7.4) is added to cells. Cells are kept for 60 min at 37° C. prior to initiating experiments and used within 5 hrs of isolation.

5B. ADULT VENTRICULAR MYOCYTE CONTRACTILITY EXPERIMENTS

Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments. To determine basal contractility, myocytes are imaged through a 40× objective and using a variable frame rate (60–240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01–15 μM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

5C. CONTRACTILITY ANALYSIS Three or more individual myocytes are tested per compound, using two or more different myocyte preparations. For each cell, ten or more contractility transients at basal (defined as 1 min. prior to compound infusion) and at 5 min. after compound addition, are averaged and compared. These average transients are analyzed to determine changes in diastolic length, and using the Ionwizard analysis program (IonOptix), fractional shortening (% decrease in the diastolic length), and maximum contraction and relaxation velocities (μm/sec) are determined. Analysis of individual cells are combined. Increase in fractional shortening over basal indicates potentiation of myocyte contractility.

5D. RESULTS Compounds of the present invention show activity when tested by this method.

Example 6

In Vivo Fractional Shortening Assay

6A. ANIMALS Male Sprague Dawley rats from Charles River Laboratories (275–350 g) are used for bolus efficacy and infusion studies. Heart failure animals are described below. They are housed two per cage and have access to food and water ad libitum. There is a minimum three-day acclimation period prior to experiments.

6B. ECHOCARDIOGRAPHY Animals are anesthetized with isoflurane and maintained within a surgical plane throughout the procedure. Core body temperature is maintained at 37° C. by using a heating pad. Once anesthetized, animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter−end systolic diameter)/end diastolic diameter× 100) is determined by analysis of the M-mode images using the GE EchoPak software program.

6C. BOLUS AND INFUSION EFFICACY For bolus injection, rats are treated as described above. Five pre-dose M-Mode images are taken at 30 second intervals prior to bolus injection or infusion of compounds. After injection, M-mode images are taken at 30 second intervals up to 10 minutes and every minute or at five minute intervals thereafter. Bolus injection or infusion is via the tail vein. Infusion parameters are determined from pharmacokinetic profiles of specific compounds.

6D. RESULTS Compounds of the present invention show activity when tested by this method.

Example 7

Left Coronary Artery Occlusion Model of Congestive Heart Failure

7A. ANIMALS Male Sprague-Dawley CD (220–225 g; Charles River) rats are used in this experiment. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study. The animals are fasted overnight prior to surgery.

7B. OCCLUSION PROCEDURE Animals are anaesthetized with ketamine/xylazine (95 mg/kg and 5 mg/kg) and intubated with a 14–16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10–15 cm $H_2O$ and respiratory rate 60–110 breaths/min. 100% $O_2$ is delivered to the animals by the ventilator. The surgical site is scrubbed with surgical scrub and alcohol. An incision is made over the rib cage at the $4^{th}$–$5^{th}$ intercostal space. The underlying muscles are dissected with care to avoid the lateral thoracic vein, to expose the intercostal muscles. The chest cavity is entered through $4^{th}$–$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The left coronary artery is occluded by tying the suture around the artery ("LCO"). Sham animals are treated the same, except that the suture is not tied. The incision is closed in three layers. The rat is ventilated until able to ventilate on its own. The rats are extubated and allowed to recover on a heating pad. Animals receive buprenorphine (0.01–0.05 mg/kg SQ) for post operative analgesia. Once awake, they are returned to their cage. Animals are monitored daily for signs of infection or distress. Infected or moribund animals are euthanized. Animals are weighed once a week.

7C. EFFICACY ANALYSIS Six weeks after surgery, rats are scanned for signs of myocardial infarction using ultrasound as described above. Only those animals with decreased fractional shortening compared to sham rats are utilized in efficacy experiments. In all experiments, there are four groups: sham+vehicle, sham+compound, LCO+vehicle, and LCO+compound. At 7–12 weeks post LCO, rats receive a bolus injection or are infused with test compound. As in Example 6, five pre-dose M-Mode images are taken at 30 second intervals prior to bolus injection or infusion of compound. After injection, M-mode images are taken at 30 second intervals up to 10 minutes, and thereafter every minute or at five minute intervals. Fractional shortening is determined from the M-mode images. Comparisons between the pre-dose fractional shortening and post compound treatment are performed by ANOVA and a post-hoc Student-Newman-Keuls with the StatView statistical program (SAS Institute). A p value <0.05 is considered significant.

7D. RESULTS Compounds of the present invention show activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:
1. A compound represented by Formula I:

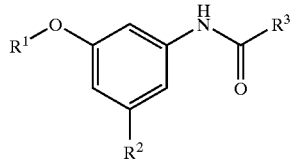

Formula I wherein:
$R^1$ is phenyl, pyridinyl, or phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, beuzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

$R^2$ is fluoro, ethoxycarbonyl, oxazolyl, pyrazinyl, pyridinyl, pyrimidinyl, tetrazolyl or thiazolyl, wherein said oxazolyl, pyrazinyl, pyridinyl, pyrimidinyl, tetrazolyl or thiazolyl is optionally substituted with lower alkoxy or oxo; and $R^3$ is aryl or heteroaryl each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

wherein said heteroaryl group is a 5-, 6- or 7-membered heteroaromatic ring containing 1–4 heteroatoms selected from O, N or S; a bicyclic 9- or 10-membered heteroaromatic ring system containing 1–4 heteroatoms selected from O, N or S; or a tricyclic 12- to 14-membered heteroaromatic ring system containing 1–4 heteroatoms selected from O, N or S, or a single stereoisomer, or mixture of stereoisomers, or a pharmaceutically acceptable salt thereof.

2. The compound of claim 1 where $R^1$ is 3-chlorophenyl, 4-fluorophenyl, 4-hydroxyphenyl, 3-methylphenyl, pyridin-2-yl, pyridin-3-yl or pyridin-4-yl.

3. The compound of claim 2 where $R^1$ is 4-fluorophenyl, pyridin-2-yl or pyridin-3-yl.

4. The compound of claim 1 where $R^3$ is phenyl, optionally substituted with lower alkoxy, lower alkyl, halo, hydroxy, hydroxy-lower alkyl or nitro.

5. The compound of claim 1 where $R^3$ is benzodioxolyl, furanyl, indolyl, isoxazolyl, pyrazolyl, pyridinyl or thienyl, optionally substituted with lower alkyl, lower alkoxy, or halo.

6. The compound of claim 3 where $R^3$ is:
phenyl, optionally substituted with lower alkoxy, lower alkyl, halo, hydroxy, hydroxy-lower alkyl or nitro; or
benzodioxolyl, furanyl, indolyl, isoxazolyl, pyrazolyl, pyridinyl or thienyl, optionally substituted with lower alkyl, lower alkoxy, or halo.

7. The compound of claim 1 or 3 where $R^3$ is 3-hydroxyphenyl, 4-hydroxyphenyl, 4-fluorophenyl, isoxazol-5-yl, pyridin-3-yl, pyridin-4-yl, thien-2-yl, or 5-methyl-thien-2-yl.

8. The compound of claim 1 where R¹ is heteroaryl and R² is fluoro.

9. The compound of claim 8 where R¹ is pyridin-3-yl.

10. The compound of claim 1 that is:
3-(4-fluoro-benzoylamino)-5-(pyridin-3-yloxy)-benzoic acid ethyl ester;
4-fluoro-N-[3-pyridin-2-yl-5-(pyridin-3-yloxy)-phenyl]-benzamide;
4-fluoro-N-[3-pyrazin-2-yl-5-(pyridin-3-yloxy)-phenyl]-benzamide;
N-[3-fluoro-5-(pyridin-3-yloxy)-phenyl]-3-hydroxy-benzamide;
N-[3-fluoro-5-(pyridin-3-yloxy)-phenyl]-4-hydroxy-benzamide;
N-[3-fluoro-5-(pyridin-3-yloxy)-phenyl]-nicotinamide; or
isoxazole-5-carboxylic acid [3-fluoro-5-(pyridin-3-yloxy)-phenyl]-amide.

11. A compound represented by Formula I:

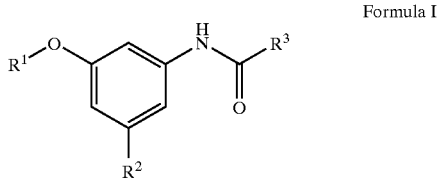

Formula I wherein:
R¹ is alkyl, aryl, or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;
R² is nitro; and
R³ is aryl, or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;
wherein said heteroaryl group is a 5-, 6- or 7-membered heteroaromatic ring containing 1–4 heteroatoms selected from O, N or S; a bicyclic 9- or 10-membered heteroaromatic ring system containing 1–4 heteroatoms selected from O, N or S; or a tricyclic 12- to 14-membered heteroaromatic ring system containing 1–4 heteroatoms selected from O, N or S,
provided that:
when R¹ is pyridin-3-yl, R³ is not 3-bromophenyl, 3-fluorophenyl, 4-fluorophenyl, furan-2-yl, 4-methoxyphenyl or 1-methyl-1H-pyrazol-3-yl;

when R¹ is 4-bydroxyophenyl, R³ is not furan-2-yl;
when R¹ is 4-fluorophenyl, R³ is not furan-2-yl or pyridin-4-yl; and
when R³ is pyridin-4-yl, R¹ is not phenyl, 3-chlorophenyl, 4-hydroxyphenyl or 3-methylphenyl;

or a single stereoisomer, or mixture of stereoisomers, or a pharmaceutically acceptable salt thereof.

12. The compound of claim 11 where R¹ is aryl or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy.

13. The compound of claim 12 where R¹ is phenyl, pyridinyl, or phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy.

14. The compound of claim 13 where R¹ is 3-chlorophenyl, 4-fluorophenyl, 4-hydroxyphenyl, 3-methylphenyl, pyridin-2-yl or pyridin-3-yl.

15. The compound of claim 14 where R¹ is 4-fluorophenyl, pyridin-2-yl or pyridin-3-yl.

16. The compound of claim 11, 14 or 15 where R³ is aril or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy.

17. The compound of claim 16 where R³ is phenyl, 4-fluorophenyl, 4-cyanophenyl, 4-methoxyphenyl, 4-methylphenyl, isoxazol-5-yl, thiophene-2-yl, or 5-methyl-thiophene-2-yl.

18. The compound of claim 11 that is:
thiophene-2-carboxylic acid [3-(4-fluoro-phenoxy)-5-nitro-phenyl-amide;
isoxazole-5-carboxylic acid [3-(4-fluoro-phenoxy)-5-nitro-phenyl-amide;
5-methyl-thiophene-2-carboxylic acid [3-nitro-5-(pyridin-3-yloxy)phenyl]-amide; or
4-fluoro-N-[3-nitro-5-(pyridin-2-yloxy)-phenyl]-benzamide.

19. A method of treatment for heart failure, comprising administering to a mammal in need thereof a therapeutically effective amount of a compound represented by Formula I:

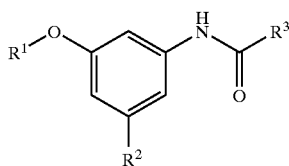

Formula I wherein:
R¹ is, phenyl, pyridinyl, or phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

R² is fluoro, ethoxycarbonyl, oxazolyl, pyrazinyl, pyridinyl, pyrimidinyl, tetrazolyl or thiazolyl, wherein said oxazolyl, pyrazinyl, pyridinyl, pyrimidinyl, tetrazolyl or thiazolyl is optionally substituted with lower alkoxy or oxo; and R³ is aryl, or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

wherein said heteroaryl group is a 5-, 6- or 7-membered heteroaromatic ring containing 1–4 heteroatoms selected from O, N or S; a bicyclic 9- or 10-membered heteroaromatic ring system containing 1–4 heteroatoms selected from O, N or S; or a tricyclic 12- to 14-membered heteroaromatic ring system containing 1–4 heteroatoms selected from O, N or S, or a single stereoisomer, or mixture of stereoisomers, or a pharmaceutically acceptable salt thereof.

20. The method of claim 19 where R¹ is 3-chlorophenyl, 4-fluorophenyl, 4-hydroxyphenyl, 3-methylphenyl, pyridin-2-yl or pyridin-3-yl.

21. The method of claim 19, or 20 where R³ is:
phenyl, optionally substituted with lower alkoxy, lower alkyl, halo (particularly bromo, chloro or fluoro), hydroxy, hydroxy-lower alkyl or nitro; or
benzodioxolyl, furanyl, indolyl, isoxazolyl, pyrazolyl, pyridinyl or thiophenyl, optionally substituted with lower alkyl, lower alkoxy, or halo.

22. The method of claim 21 where R³ is 3-hydroxyphenyl, 4-hydroxyphenyl, 4-fluorophenyl, isoxazol-5-yl, pyridin-3-yl, pyridin-4-yl, thiophen-2-yl or 5-methyl-thiophen-2-yl.

23. The method of claim 19 where R¹ is phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy and R² is nitro.

24. The method of claim 23 where where R¹ is 4-fluorophenyl.

25. The method of claim 19 where R¹ is heteroaryl and R² is fluoro.

26. The method of claim 25 where where R¹ is pyridin-3-yl.

27. The method of claim 19 where R¹ is heteroaryl.

28. The method of claim 27 where where R¹ is pyridin-3-yl.

29. The method of claim 28 where R³ is phenyl, 4-fluorophenyl, 4-cyanophenyl, 4-methoxyphenyl or 4-methylphenyl.

30. The method of claim 19 comprising a method of treating a heart disease that is associated with systolic dysfunction.

31. The method of claim 19 where the compound is:
4-fluoro-N-[3-(pyridin-3-yloxy)-5-trifluoromethyl-phenyl]-benzamide;
5-methyl-thiophene-2-carboxylic acid [3-nitro-5-(pyridin-3-yloxy)phenyl]-amide;
4-fluoro-N-[3-pyridin-2-yl-5-(pyridin-3-yloxy)-phenyl]-benzamide;
4-fluoro-N-[3-pyrazin-2-yl-5-(pyridin-3-yloxy)-phenyl]-benzamide;
4-fluoro-N-[3-nitro-5-(pyridin-2-yloxy)-phenyl]-benzamide;
N-[3-fluoro-5-(pyridin-3-yloxy)-phenyl]-3-hydroxy-benzamide;
N-[3-fluoro-5-(pyridin-3-yloxy)-phenyl]-4-hydroxy-benzamide;
N-[3-fluoro-5-(pyridin-3-yloxy)-phenyl]-nicotinamide; or
isoxazole-5-carboxylic acid [3-fluoro-5-(pyridin-3-yloxy)-phenyl)-amide.

32. A pharmaceutical formulation comprising a pharmaceutically accepted excipient and a therapeutically effective amount of a compound represented by Formula I:

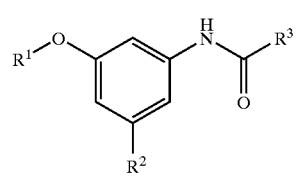

Formula I wherein:
R¹ is phenyl, pyridinyl, or phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

R² is fluoro, ethoxycarbonyl, oxazolyl, pyrazinyl, pyridinyl, pyrimidinyl, tetrazolyl or thiazolyl, wherein said oxazolyl, pyrazinyl, pyridinyl, pyrimidinyl, tetrazolyl or thiazolyl is optionally substituted with lower alkoxy or oxo; and R³ is aryl, or heteroaryl, each of which is optionally substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy;

wherein said heteroaryl group is a 5-, 6- or 7-membered heteroaromatic ring containing 1–4 heteroatoms selected from O, N or S; a bicyclic 9- or 10-membered heteroaromatic ring system containing 1–4 heteroatoms selected from O, N or S; or a tricyclic 12- to 14-membered heteroaromatic ring system containing 1–4 heteroatoms selected from O, N or S, or a single stereoisomer, or mixture of stereoisomers, or a pharmaceutically acceptable salt thereof.

33. The pharmaceutical formulation of claim 32 where $R^1$ is phenyl substituted with alkyl, halogen, hydroxy, alkoxy, alkylenedioxy, fluoroalkyl, carboxy, carboalkoxy, carboxyalkyl, carboxamido, sulfonamidoalkyl, sulfonamidyoaryl, aminocarbonyl, benzyloxycarbonylamino, cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, phenoxy, benzyloxy, or heteroaryloxy and $R^2$ is nitro.

34. The pharmaceutical formulation of claim 33 where where $R^1$ is 4-fluorophenyl.

35. The pharmaceutical formulation of claim 32 where $R^1$ is heteroaryl and $R^2$ is fluoro.

36. The pharmaceutical formulation of claim 35 where where $R^1$ is pyridin-3-yl.

37. The pharmaceutical formulation of claim 32 where $R^1$ is heteroaryl.

38. The pharmaceutical formulation of claim 37 where where $R^1$ is pyridin-3-yl.

39. The pharmaceutical formulation of claim 38 where $R^3$ is phenyl, 4-fluorophenyl, 4-cyanophenyl, 4-methoxyphenyl or 4-methylphenyl.

40. The pharmaceutical formulation of claim 32 where the compound is:
    N-[3-cyano-5-(pyridin-3-yloxy)-phenyl]]-4-fluoro-benzamine;
    4-fluoro-N-[3-(pyridin-3-yloxy)-5-trifluoromethyl-phenyl]-benzamide;
    5-methyl-thiophene-2-carboxylic acid [3-nitro-5-(pyridin-3-yloxy)phenyl]-amide;
    4-fluoro-N-[3-pyridin-2-yl-5-(pyridin-3-yloxy)-phenyl]-benzamide;
    4-fluoro-N-[3-pyrazin-2-yl-5-(pyridin-3-yloxy)-phenyl]-benzamide;
    4-fluoro-N-[3-nitro-5-(pyridin-2-yloxy)-phenyl]-benzamide;
    N-[3-fluoro-5-(pyridin-3-yloxy)-phenyl]-3-hydroxy-benzamide;
    N-[3-fluoro-5-(pyridin-3-yloxy)-phenyl]-4-hydroxy-benzamide;
    N-[3-fluoro-5-pyridin-3-yloxy)-phenyl]-nicotinamide; or
    isoxazole-5-carboxylic acid [3-fluoro-5-(pyridin-3-yloxy)-phenyl)-amide.

41. The compound of claim 1 wherein $R^2$ is oxazol-2-yl, pyrazin-2-yl, pyridin-1-yl, pyridin-2-yl, pyrimidin-2-yl, tetrazol-2-yl, or thiazol-2-yl.

42. The compound of claim 41 wherein $R^2$ is 3-methoxy-2-oxo-2H-pyridin-1-yl.

43. The compound of claim 41 wherein $R^2$ is 1-methoxymethoxy-1H-tetrazol-5-yl, or 2-methoxymethoxy-2H-tetrazol-5-yl.

* * * * *